US00PP11305P

United States Patent [19]

Brown et al.

[11] Patent Number: Plant 11,305

[45] Date of Patent: Mar. 21, 2000

[54] AGLAONEMA PLANT NAMED 'PEACOCK'

[75] Inventors: B. Frank Brown; Cleofar P. Millare, both of Valkaria, Fla.

[73] Assignee: Sunshine Foliage World, Zolfo Springs, Fla.

[21] Appl. No.: 09/114,115

[22] Filed: Jul. 13, 1998

[51] Int. Cl.[7] ..... A01H 5/00

[52] U.S. Cl. ..... Plt./376

[58] Field of Search ..... Plt./376

[56] References Cited

U.S. PATENT DOCUMENTS

P.P. 9,081 3/1995 Button et al. ..... Plt./376

*Primary Examiner*—Howard J. Locker
*Assistant Examiner*—Kent L. Bell
*Attorney, Agent, or Firm*—C. A. Whealy

[57] ABSTRACT

A new and distinct cultivar of Aglaonema named 'Peacock' particularly characterized by its mostly upright and somewhat outwardly arching plant habit; upper mature leaf surfaces that are mottled silver green with random dark green spots with yellow-green midrib giving a tricolor appearance; leaf shape that is oblong and narrow with recurved apex; light green to white petioles with occasional green spots and streaks; excellent tolerance to low temperatures; and resistance to diseases common to Aglaonema.

1 Drawing Sheet

BACKGROUND OF THE INVENTION

The present invention relates to a new and distinct cultivar of Aglaonema plant, botanically known as Aglaomena hybrid, and hereinafter referred to by the cultivar name 'Peacock'.

The new Aglaonema is a product of a planned breeding program conducted by the Inventors in Valkaria, Fla. The objective of the breeding program was to develop new Aglaonemas with unique and interesting leaf patterns that readily produced divisions. The new Aglaonema originated from a cross made by the Inventors of the *Aglaonema marantifolium* cv. 'Tricolor' (not patented) as the male, or pollen, parent with the *Aglaonema commutatum* var. *picturatum* cv. 'Echo' (not patented) as the female, or seed, parent. The cultivar 'Peacock' was discovered and selected by the Inventors in March, 1987 as a seedling within the progeny of the stated cross in a controlled environment in Valkaria, Fla.

Plants of the new Aglaonema differ from plants of the male parent, the cultivar 'Tricolor', in leaf color, leaf pattern, midrib color and petiole color. Plants of the new Aglaonema differ from plants of the female parent, the cultivar 'Echo' in leaf shape, leaf size, leaf color, leaf pattern, petiole color, plant form and tolerance to low temperatures.

Asexual propagation of the new cultivar by divisions at Valkaria and Zolfo Springs, Fla. has shown that the unique features of this new Aglaonema plant are stable and reproduced true to type in successive generations.

SUMMARY OF THE INVENTION

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Peacock'. These characteristics in combination distinguish 'Peacock' as a new and distinct cultivar:

1. Plants of the new Aglaonema are mostly upright and somewhat outwardly arching in plant habit.

2. Plants of the new Aglaonema typically grow to about 1 meter in height.

3. Plants of the new Aglaonema readily produce divisions.

4. The upper surfaces of mature leaves of plants of the new Aglaonema are mottled silver green with random dark green spots with yellow-green midrib giving a tricolor appearance.

5. The leaves of the new Aglaonema are oblong and narrow with recurved apex.

6. Leaves of plants of the new Aglaonema have light green to white petioles with occasional green spots and streaks.

7. Plants of the new Aglaonema are very tolerant of low temperatures, that is, ambient temperatures of about 2° C. do not cause foliar damage.

8. Plants of the new Aglaonema are resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Peacock' in a 35-cm container.

The photograph at the bottom of the sheet comprises a close-up view of the upper and lower surfaces of mature leaves. Leaf colors in the photographs may appear different from the actual colors due to light reflectance.

DETAILED BOTANICAL DESCRIPTION

The following observations, measurements and comparisons describe plants grown in Zolfo Springs, Fla. under a polypropylene-covered shadehouse and conditions which closely approximate those used in horticultural practice. Plants were grown under day temperatures ranging from 21 to 38° C. and night temperatures ranging from 7 to 21° C.

The polypropylene shade provided a 84 percent decrease in ambient light level. In the following description, color references are made to The Royal Horticultural Society Colour Chart except where general terms of ordinary dictionary significance are used.

Botanical classification: Aglaonema hybrid cultivar 'Peacock'.

Parentage:

*Male, or pollen, parent.*—*Aglaonema marantifolium* cultivar 'Tricolor'.

*Female, or seed, parent.*—*Aglaonema commutatum* var. *picturatum* cultivar 'Echo'.

Propagation:

*Type.*—By division and by cuttings.

*Time to initiate roots.*—About 24 and 42 days at 30 and 20° C., respectively.

*Time to develop roots.*—About 30 and 60 days at 30 and 20° C., respectively.

*Rooting habit.*—Branching fleshy and fibrous roots.

Plant description:

*Plant shape.*—Mostly upright and somewhat outwardly arching.

*Growth habit.*—Erect when young, becoming outwardly arching. Appropriate for 25.5-cm and larger containers. Plants readily produce divisions.

*Plant size.*—Height, soil surface to top of leaf canopy: About 72 cm. Width: About 72 cm.

*Plant vigor.*—Moderate to vigorous.

*Stem description.*—Diameter at soil surface: About 2.75 cm. Internode length: About 1.75 cm. Color, mature: Light yellowish green.

*Foliage description.*—Shape: Oblong, narrow. Length, fully expanded: About 32.5 cm. Width, fully expanded: About 11.5 cm. Margin: Entire. Apex: Acuminate, recurved. Base: Obtuse to slightly cordate. Aspect: Mostly flat, undulate. Texture: Leathery, smooth, glabrous, some gloss on both surfaces. Color: Young, upper surface: Background: Light green, close to 147C/138B. Green spots/streaks; Greener than 143A and darker than 144A. White and yellow spots: Near to midvein, 154D to 145D to 155D. Midvein: Yellowish to whitish green, 154A to 154D, 145C, and 145D. Young, lower suface: Background: Close to 146B. Lateral veins: Whitish green, close to 145D. Midvein: 147C, 146D, and 147D. Mature, upper surface: Background: Mottled silver green, 189A, 189B, and 191A. Dark green spots: Darker than 147A. Green spots: Darker than 146A. White and light green spots/streaks: 145D to 155D. Midvein: Mostly yellowish green spots, 154A, to 154D. Mature, lower surface: Background: Close to 143A/144A. Lateral veins: Whitish green, 145D. Midvein: Whitish green, 145D, to white, 155D. Petiole length, primary shoot: About 28 cm. Petiole diameter at apex: About 6 mm. Petiole diameter at base: About 2.1 cm. Petiole wing: Apparent on lower 35 percent of mature leaf petiole, about 10 cm in length and about 5 mm in width. Petiole color: Whitish green, 145D, to white, 155D, with green, 143A to 144A spots and streaks.

*Inflorescence.*—Typical of Aglaonema, no commerical significance.

Disease tolerance: Plants of the new Aglaonema are resistant to diseases common to Aglaonema.

Low temperature tolerance: Plants of the new Aglaonema are very tolerant of low temperatures, that is, ambient temperatures of about 2° C. do not cause foliar damage.

It is claimed:

1. A new and distinct cultivar of Aglaonema plant named 'Peacock', as illustrated and described.

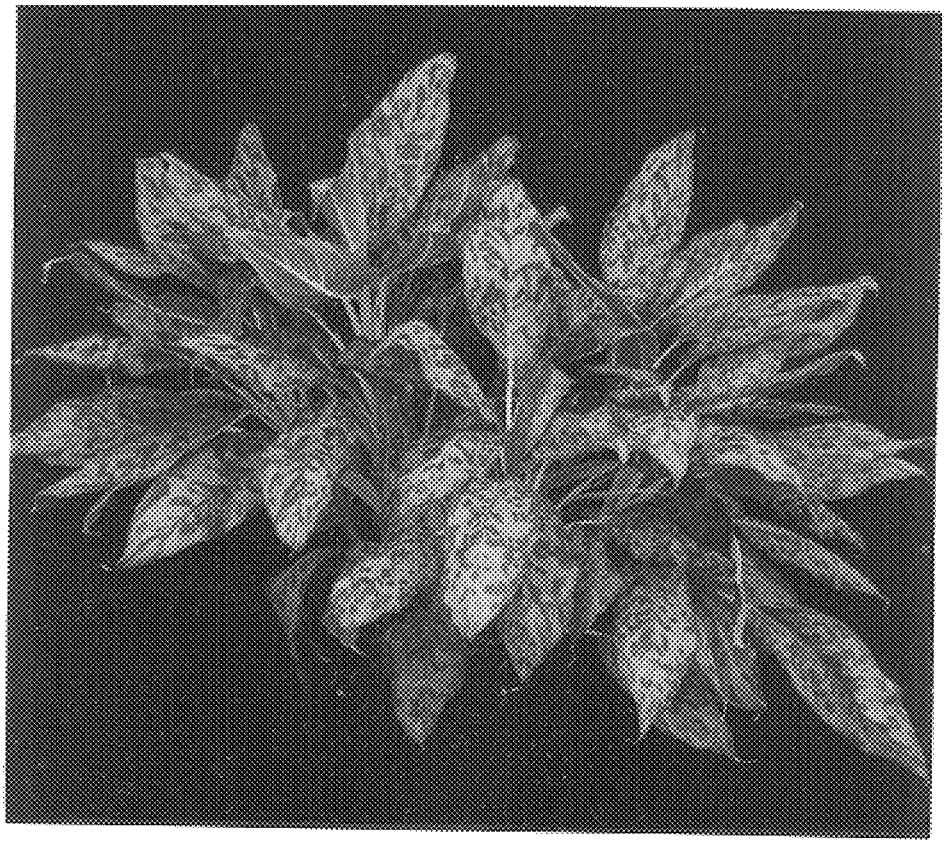
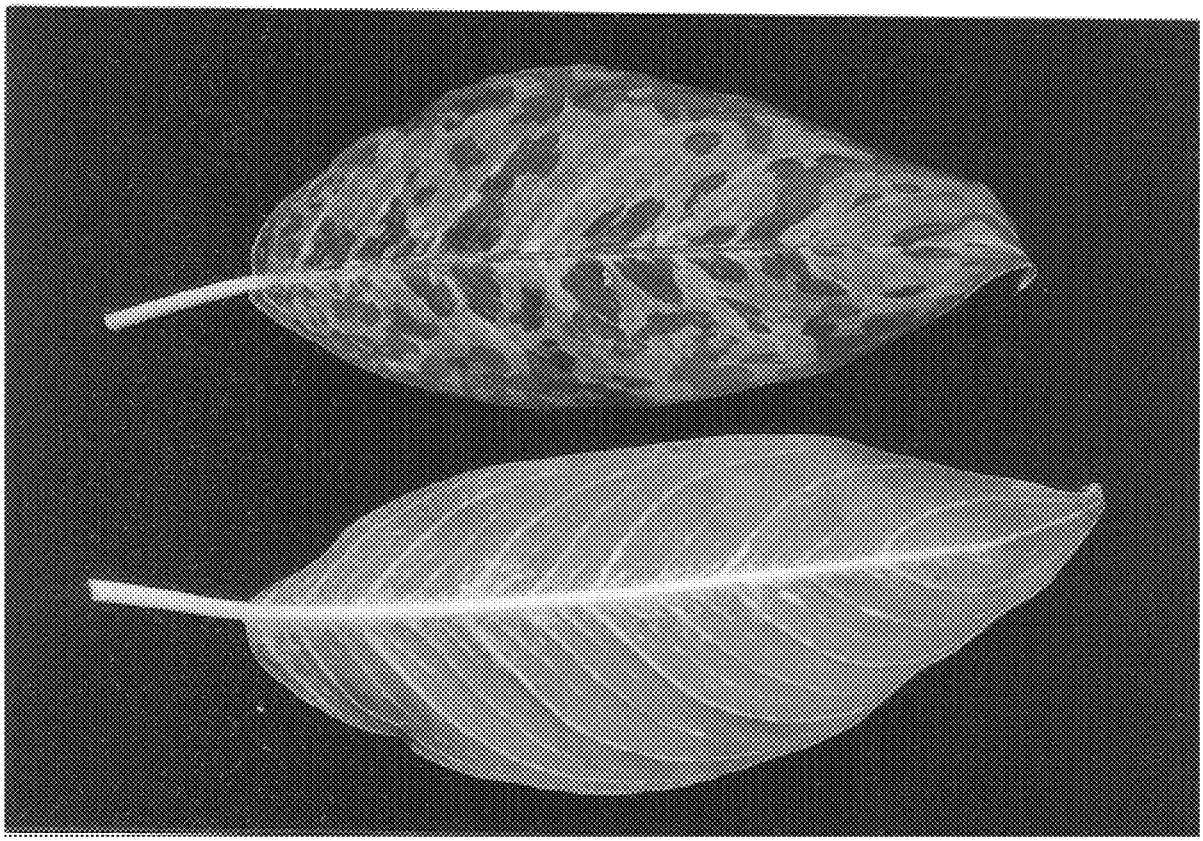

* * * * *